United States Patent [19]
Smith

[11] Patent Number: 5,935,937
[45] Date of Patent: Aug. 10, 1999

[54] COMPOSITIONS AND METHODS FOR INDUCING APOPTOSIS

[75] Inventor: Mitchell R. Smith, Elkins Park, Pa.

[73] Assignee: Fox Chase Cancer Center, Philadelphia, Pa.

[21] Appl. No.: 08/877,831

[22] Filed: Jun. 18, 1997

Related U.S. Application Data

[60] Provisional application No. 60/020,072, Jun. 19, 1996.

[51] Int. Cl.$^6$ ........................... C07H 21/04; A61K 48/00
[52] U.S. Cl. ........................... 514/44; 435/6; 435/172.3; 435/320.1; 536/23.1; 536/24.1; 536/24.5
[58] Field of Search ........................ 435/6, 172.1, 172.3, 435/320.1; 514/44; 536/23.1, 24.1, 24.5

[56] References Cited

U.S. PATENT DOCUMENTS 5,585,479  12/1996  Hoke et al. ............................. 536/24.5

OTHER PUBLICATIONS

M. Smith et al., Cancer Gene Therapy, 2(3): 207–212 (1995).

M. Crescenzi et al., Proc. Natl. Acad. Sci. USA, 85: 4869–4873 (1988).

H. Dorai et al., Nucleic Acids Research, 17(15): 6412 (1989).

M. Seto et al., The EMBO Journal, 7(1): 123–131 (1988).

M. Cleary et al., Cell, 47: 19–28 (1986).

F. Keith et al., Leukemia, 9: 131–138 (1995).

S. Kitada et al., Antisense Research and Development, 4: 71–79 (1994).

Stull et al "Antigene, Ribozyme and Aptamer Nucleic Acid Drugs: Progress and Prospects" Pharmaceutical Research vol. 12(4)485–483 1995.

*Primary Examiner*—Nancy Degen
*Assistant Examiner*—Sean McGarry
*Attorney, Agent, or Firm*—Dann, Dorfman, Herrell and Skillman

[57] ABSTRACT

Compositions and methods for the treatment of malignant cells are disclosed, particularly antisense nucleic acid molecules and their use in inhibiting the deregulated cellular proliferation of tumor cells, while not adversely affecting the growth of normal cells.

10 Claims, 4 Drawing Sheets

DNA CONTENT

DNA CONTENT

COMPOSITIONS AND METHODS FOR INDUCING APOPTOSIS

This application claims benefit of provisional application 60/020,072 filed Jun. 19, 1996 under 35 U.S.C. § 119(e).

FIELD OF THE INVENTION

This invention relates to the field of molecular biology and in particular to compositions and methods for inducing programmed cell death. Specifically, the invention provides antisense nucleic acid molecules which induce apoptosis in malignant cells.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Apoptosis is a type of cell death that appears to be under direct genetic control. During apoptosis, cells lose their cell junctions and microvilli. The cytoplasm condenses and nuclear chromatin marginates into a number of discrete masses. While the nucleus fragments, the cytoplasm contracts and mitochondria and ribosomes become densely compacted. After dilation of the endoplasmic reticulum and its fusion with the plasma membrane, the cell breaks up into several membrane bound vesicles, also known as apoptotic bodies, which are usually phagocytosed by adjacent cells.

Apoptosis induced by numerous cytotoxic agents can be suppressed by expression of the gene bcl-2 which produces a cytoplasmic protein BCL2. The bcl-2 gene was initially cloned from the t(14,18) (q32,q21) breakpoint commonly found in follicular lymphomas (1–3). BCL2 protein prevents programmed cell death in a number of systems, including B-lymphocytes. Bcl-2 appears to be expressed primarily in tissues in which cells undergo apoptosis. Transgenic mice experiments suggest that bcl-2 plays a physiologic role in T-lymphocyte selection in the thymus.

Low grade non-Hodgkin's lymphomas, including most follicular lymphomas, are considered incurable with current therapy, although bone marrow transplantation may alter this outlook for selected patients. The follicular lymphomas are characterized (85–90% of cases) by the chromosomal translocation t(14,18), in which the breakpoint on chromosome 18 is in the 3' untranslated portion of the bcl-2 gene and that on chromosome 14 is in the immunoglobulin heavy chain J region. These are joined in a head-to-tail fashion and result in a fusion messenger RNA encoding a full-length BCL2 gene product with altered regulation, generally highly expressed due to the attached immunoglobulin gene. BCL2 has oncogenic properties. Transgenic mice that overexpress the bcl-2/immunoglobulin fusion gene accumulate large numbers of small B-lymphocytes and in many ways mimic low-grade lymphoma, supporting the concept that dysregulated expression of this fusion gene is important in the pathogenesis of follicular lymphoma.

Growth inhibition by down-regulation of bcl-2 with antisense oligonucleotides specific for the bcl-2 promoter region has previously been reported (4–6). However, in vivo, it is not always optimal to target oncogenic sequences for antisense therapy due to non-specific deleterious effects on normal cells. Thus, there continues to be considerable research activity relating to antisense molecules specific for sequences at chromosomal translocation breakpoints present in various malignant tumors. An important goal of such research is to inhibit aberrant cellular proliferation by targeting such breakpoints. To date, targeting the non-oncogenic sequences of fusion transcripts so as to expand the potential for tumor specific genetic manipulation has not yet been explored.

SUMMARY OF THE INVENTION

According to one aspect of the present invention, a method is provided for inhibiting production of a predetermined fusion protein in a living organism. The method comprises providing an antisense oligonucleotide or a vector encoding antisense RNA molecules which are capable of binding specifically to a specified sequence of a fusion gene and/or its mRNA fusion transcript. The antisense oligonucleotide is administered to the living organism under conditions whereby the oligonucleotide enters cells expressing the fusion gene and binds specifically to a targeted sequence of the nucleic acid encoding the fusion protein, in an amount sufficient to control the production of the fusion protein and/or induce apoptosis in a malignant cell. In a preferred embodiment, antisense oligonucleotides are targeted 3' to the chromosomal breakpoint in the fusion transcript.

According to another aspect of the present invention, there is provided an antisense oligonucleotide that is useful for decreasing production of a bcl2-Ig fusion protein in a living organism. The antisense oligonucleotide of the invention is capable of entering a cell producing such a fusion protein and binding specifically to the nucleic acid (fusion gene or its mRNA transcript) that encodes the fusion protein, in an amount sufficient to control expression of the fusion gene.

In a preferred embodiment of the present invention, the antisense oligonucleotide is an oligonucleotide analog having improved stability and membrane permeability as compared with an unmodified oligonucleotide. According to one aspect, stability of the antisense analog is enhanced by using phosphorothioate modification. Other modifications may include peptide nucleic acids, methylphosphonates and/or 2-O-methyl ribonucleic acids.

According to another aspect of the present invention, a method is provided for treating a pathological condition related to the expression of a fusion gene. Examples of such pathological conditions are certain non-Hodgkin's lymphomas and other follicular lymphomas. The method comprises administering to a patient having such a pathological condition a pharmaceutical preparation comprising an antisense oligonucleotide analog capable of entering a cell expressing the fusion gene and binding specifically to a nucleic acid encoding the fusion protein, in an amount sufficient to affect the level of production of the encoded fusion protein, thereby alleviating the pathological condition.

According to another aspect of this invention, a pharmaceutical preparation is provided for treating a pathological condition related to the aberrant expression of a fusion gene. This pharmaceutical preparation comprises, in a biologically compatible medium, an antisense oligonucleotide capable of entering a cell expressing the fusion gene and binding specifically to a nucleic acid encoding the fusion protein in an amount sufficient to adversely affect the level of expression of the fusion gene. Incorporation of the antisense analogs into a lipophilic delivery system for enhanced delivery is also contemplated to be within the scope of this invention.

According to a further aspect of the invention, an antisense RNA molecule is delivered by a DNA vector containing sequences that encode the antisense RNA. The use of double-stranded DNA as a delivery vehicle exploits the greater natural stability of double-stranded as compared to single-stranded nucleic acids. The use of an expression vector that generates multiple RNA copies prolongs expression of the antisense RNA molecules in vivo.

Both the antisense oligonucleotide analog and the DNA expression vector encoding the antisense RNA are synthesized so as to be capable of crossing a biological membrane in order to enter cells. The DNA vector must enter the nuclear compartment such that antisense RNA is expressed. In either case, once the input nucleic acid molecules gain entry into the appropriate cellular compartment antisense oligonucleotide analogs and antisense RNA molecules will hybridize specifically with the selected nucleic acid sequence. The selected nucleic acid sequence preferably comprises specified sequences adjacent to a chromosomal translocation breakpoint. The biologically compatible medium is preferably formulated to enhance the lipophilicity and membrane-permeability of the antisense oligonucleotide or plasmid expression vector.

In yet another preferred embodiment, the antisense oligonucleotides of the invention may also be used alone or in combination with chemotherapeutic drugs to purge bone marrow or peripheral stem cell grafts of malignant cells.

BRIEF DESCRIPTION OF THE DRAWINGS

FIG. 1 A shows the effects of antisense to BCL-2. FIG. 1B shows the effects of antisense to JH. FIG. 1C shows the effects of antisense to $C\mu$.

FIG. 3 is a series of graphs (A–F) showing the flow cytometric analysis of DNA content per cell following treatment with the indicated oligonucleotides.

DETAILED DESCRIPTION OF THE INVENTION

The present invention provides compositions and methods for use in treating malignancy. In accordance with the invention, it has been discovered that fusion transcripts generated by the translocation of chromosomal segments are suitable targets for antisense therapy. Targeting sequences adjacent to the chromosomal breakpoint with antisense molecules induces apoptosis and subsequent cell death. Targeting sequences within the non-oncogenic fusion partner that is juxtaposed to an oncogene following chromosomal translocation, rather than the mRNA start site, eliminates deleterious non-specific effects on normal cells. Further, the antisense molecules will optimally be targeted to sequences downstream of the breakpoint, as the breakpoint region may be more variable among patients or may lie in a region of the transcript that is not as accessible to the antisense molecule. Additional tumor specific fusion transcripts are currently being identified. See Table III. Targeting these fusion transcripts with antisense molecules for therapeutic treatment is also contemplated to be within the scope of this invention.

Specific genetic abnormalities represent targets for novel therapeutic strategies in the treatment of malignancies. The chromosomal translocation t(14;18)(q32;q21) is the most common genetic abnormality in non-Hodgkin's lymphoma (7). This translocation results in a fusion transcript containing the entire bcl-2 coding sequence with a 3' breakpoint fused to the immunoglobulin $J_H$ region (7–10). These immunoglobulin sequences serve as a specific target for down-regulation of the fusion gene. Antisense oligodeoxyribonucleotides directed at the bcl-2 translational start site down-regulate bcl-2 expression and inhibit growth of the t(14;18) positive lymphoma line WSU-FSCCL (6). As hypothesized, it has been found in accordance with the instant invention that antisense oligodeoxyribonucleotides targeted to the fused, non-oncogenic immunoglobulin sequences can be as active as those targeted to the translation initiation site of bcl-2 in decreasing BCL2 protein production and inducing apoptosis. Such targeting should be t(14;18) specific and adversely affect the growth of malignant lymphoma cells.

Although the present invention is described with particular emphasis on targeting of bcl-2/Ig fusion transcripts, other fusion transcripts may be utilized in the practice of the instant invention as will appear in Table III, below.

SELECTION AND PREPARATION OF ANTISENSE OLIGONUCLEOTIDES AND VECTORS

Antisense oligonucleotides targeted to any known nucleotide sequence can be prepared by oligonucleotide synthesis according to standard methods. Synthesis of oligonucleotides via phosphoramidite chemistry is preferred, since it is an efficient method for preparing oligodeoxynucleotides, as well as being adapted to many commercial oligonucleotide synthesizers.

Selection of a suitable antisense sequence depends on knowledge of the nucleotide sequence of the target mRNA, or gene from which the mRNA is transcribed. Although targeting to mRNA is preferred and exemplified in the description below, it will be appreciated by those skilled in the art that other forms of nucleic acid, such as pre-mRNA or genomic DNA, may also be targeted.

In a preferred embodiment, the sequence adjacent to the translocation breakpoint of a mature mRNA encoding a fusion protein is selected as the target sequence.

Synthetic antisense oligonucleotides should be of sufficient length to hybridize to the target nucleotide sequence and exert the desired effect, i.e., blocking translation of an mRNA molecule. However, it should be noted that shorter oligonucleotides are likely to be more efficiently taken up by cells in vivo, such that a greater number of antisense oligonucleotides may be delivered to the location of the target mRNA. Preferably, antisense oligonucleotides should be at least 15 nucleotides in length, to achieve adequate specificity. Exemplified below is a 17-nucleotide antisense molecule which has been utilized for this purpose. As will appear in the following description, this oligonucleotide is complementary to the coding strand of sequences adjacent to the translocation breakpoint of the bcl-2/Ig fusion gene.

Oligonucleotides in an unprotected and native nucleic acid conformation are highly susceptible to degradation by assorted nucleases. Moreover, such molecules may be unable to enter cells because of insufficient membrane permeability. For these reasons, those skilled in the art generally synthesize oligonucleotides that are modified in various ways to increase stability and membrane permeability. The use of modified antisense oligonucleotides is preferred in the present invention. The term "antisense oligonucleotide analog" refers to such modified oligonucleotides as discussed hereinbelow.

Several methods of modifying oligonucleotides to produce stable, membrane-permeable oligonucleotide analogs are commonly known in the art. For a review see Cohen, J. S. (ed.) *Oligodeoxynucleotides: Antisense Inhibitors of Gene Expression*, CRC Press, Inc., Boca Raton, Fla. (1989). Modified oligoribonucleotides may also be utilized in the present invention. Oligodeoxyribonucleotides are preferred, however, due to enhanced stability, ease of manufacture and the variety of methods available for analog synthesis.

The oligonucleotide modification which is utilized in a preferred embodiment of the present invention, is the oligodeoxynucleotide phosphorothioate. In this DNA analog, one of the phosphate oxygen atoms not involved in the phosphate bridge is replaced by a sulphur atom, resulting in the negative charge being distributed asymmetrically and located mainly on the sulphur atoms. When compared to unmodified oligonucleotides, oligonucleotide phosphorothioates are improved with respect to stability to nucleases, retention of solubility in water and stability to base-catalyzed hydrolysis.

Another common oligonucleotide modification is the methylphosphonate backbone linkage wherein the negative charge on the inter-nucleotide phosphate bridge is eliminated by replacing the negatively charged phosphate oxygen with a methyl group. Methylphosphonate linkages also provide resistance to certain nucleases.

2'-O-methyl (ribose-modified) oligonucleotides are also suitable for the practice of the invention. The 2'-O-methyl sugar modification can be associated with any of the backbone linkages, including phosphorothioates, and the modification can be limited to the ends of the oligonucleotide.

Deoxyribonucleotide dithioates (phosphorodithioate DNA) may also be utilized in this invention. These compounds which have nucleoside-$OPS_2P$-nucleoside linkages, are phosphorous, achiral, anionic, and are thus similar to natural DNA. They form duplexes with unmodified complementary DNA. They also activate RNAse H and are resistant to nuclease, making them potentially useful as therapeutic agents. One such compound has been shown to inhibit HIV-1 reverse transcriptase (11).

Still other modifications of the oligonucleotides may include coupling the antisense oligonucleotide to sequences that code for the enzyme RNase H. RNase H will hydrolyze the RNA in the hybrid formed by the oligonucleotide and its specific mRNA target. Alkylating derivatives of oligonucleotides and derivatives containing lipophilic groups can also be used. Alkylating derivatives form covalent bonds with the mRNA, thereby inhibiting their ability to translate proteins. Lipophilic derivatives of oligonucleotides will increase their membrane permeability, thus enhancing penetration into cells.

The sequences that direct the synthesis of antisense RNA may be incorporated into a variety of viral vectors. Adenovirus or adeno-associated virus (AAV) vectors may be utilized where transient treatment is desired, as these types of vectors do not propagate and are cleared from the body with time. Adenoviral vectors are capable of efficiently transferring exogenous DNA to both proliferating and non-proliferating cells. Once localized in the nucleus, these vectors do not integrate into the cellular chromosomes; they function epi-chromosomally to express the new gene, in this case, an antisense RNA. The epi-chromosomes are not replicated during cell division, thus diminishing the presence of the antisense vector and the expression of the antisense RNA. Accordingly such vectors need to be readministered to maintain persistent expression and function. Such re-administration frequently results in an immune response which inhibits further entry into target cells. However, the objective of this invention is to induce apoptosis-mediated cell death of malignant cells, as opposed to prolonged maintenance of epi-chromosomal antisense vectors in dividing tumor cells. AAV are suitable for developing viral vectors, because they are nonpathogenic parvoviruses which are incapable of autonomous replication and spread.

ADMINISTRATION OF ANTISENSE OLIGONUCLEOTIDES

Antisense oligomers as described herein are generally administered to a patient as a pharmaceutical preparation. The term "patient" as used herein refers to human and animal subjects.

The pharmaceutical preparation comprising the antisense oligomers of the invention are conveniently formulated for administration with an acceptable medium such as water, buffered saline, ethanol, polyol (for example, glycerol, propylene glycol, liquid polyethylene glycol, and the like), dimethyl sulfoxide (DMSO), oils, detergents, suspending agents or suitable mixtures thereof. The concentration of antisense oligonucleotides in the chosen medium will depend on the hydrophobic or hydrophilic nature of the medium, as well as the length and other properties of the antisense molecule. Solubility limits may be easily determined by one skilled in the art.

As used herein, "biologically acceptable medium" includes any and all solvents, dispersion media and the like which may be appropriate for the desired route of administration or the pharmaceutical preparation, as exemplified in the preceding paragraph. The use of such media for pharmaceutically active substances is known in the art. Except insofar as any conventional media or agent is incompatible with the antisense molecules to be administered, its use in the pharmaceutical preparation is contemplated.

Selection of a suitable pharmaceutical preparation depends upon the method of administration chosen. For example, antisense oligonucleotides to non-oncogenic fusion sequences or vectors encoding antisense RNAs to such sequences, may be administered for treatment of malignant cells or tumors by direct injection into the peritoneum or bloodstream.

Pharmaceutical preparations for parenteral injection are known in the art. If parenteral injection is selected as a method for administering the antisense oligonucleotides, steps must be taken to ensure that sufficient amounts of the molecules reach their target cells to exert a biological effect. For example, when certain tissues are targeted, the lipophilicity of the antisense molecules, or the pharmaceutical preparation in which they are delivered may have to be increased so as to arrive at their target locations. Furthermore, the antisense molecules may have to be delivered in a cell-targeting carrier so that sufficient numbers of molecules will reach the target cells. Methods for increasing the lipophilicity of a molecule are known in the art, and include the addition of lipophilic groups to the antisense oligonucleotides.

Several techniques have been used to increase the stability, cellular uptake, and biodistribution of oligonucleotides. Antisense oligomers of the present invention may be encapsulated in a lipophilic targeted carrier such as a liposome. A suitable carrier for the oligonucleotide is a lipophilic preparation, such as that containing the cationic lipid N-[1-(2,3-dioleylozy)propyl]-N,N,N-trimethyl ammonium chloride (DOTMA; lipofectin). To further facilitate targeting of the antisense oligonucleotides, antibody studded liposomes may be utilized. The antibody mediates the targeting of the antisense construct to the desired tissue type and the liposome moiety mediates the membrane fusion event necessary for the construct to enter the target cell.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the antisense oligonucleotides may be administered at appropriate intervals, for example, twice a day until the pathological symptoms are reduced or alleviated, after which the dosage may be reduced to a maintenance level. The appropriate interval in a particular case would normally depend on the condition of the patient.

The following examples provide illustrative methods of practicing the instant invention, and are not intended to limit the scope of the invention in any way.

EXAMPLE I

Figure 1A:
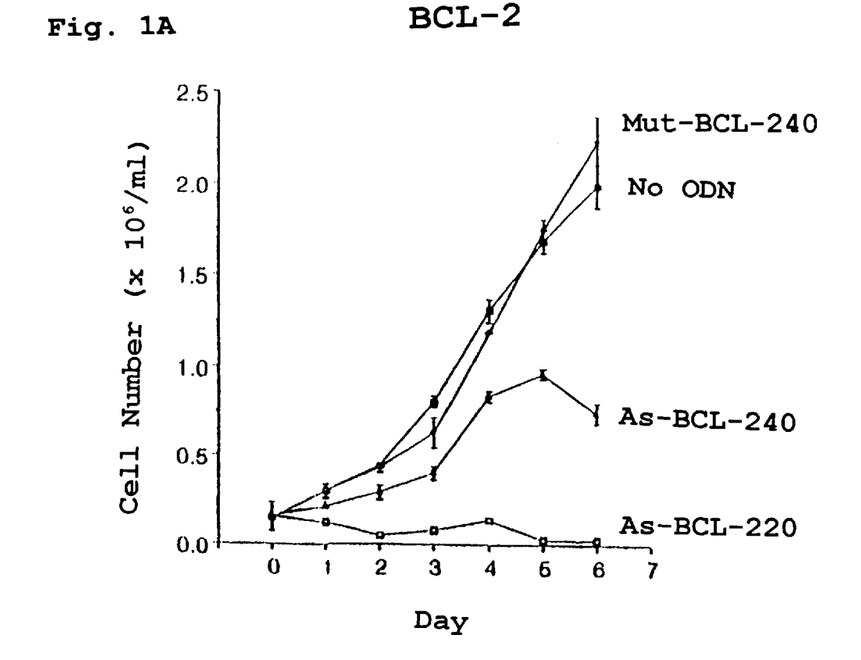
FIGS. 1A–1C are a series of graphs showing the effects of indicated oligonucleotides on the growth of a cell line, WSU-FSCCL, established from a patient with follicular small cleaved cell lymphoma at Wayne State University.
Figure 1B:
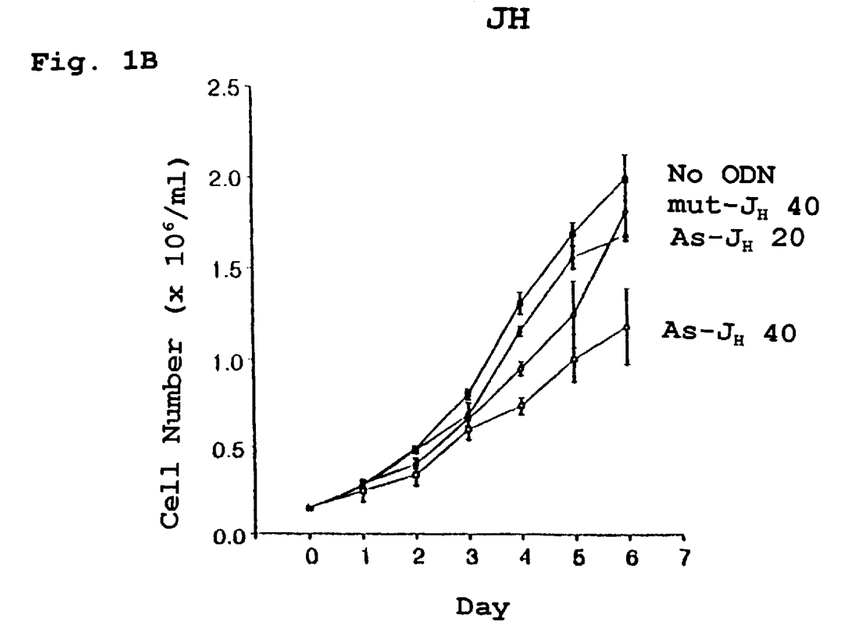
Figure 1C:
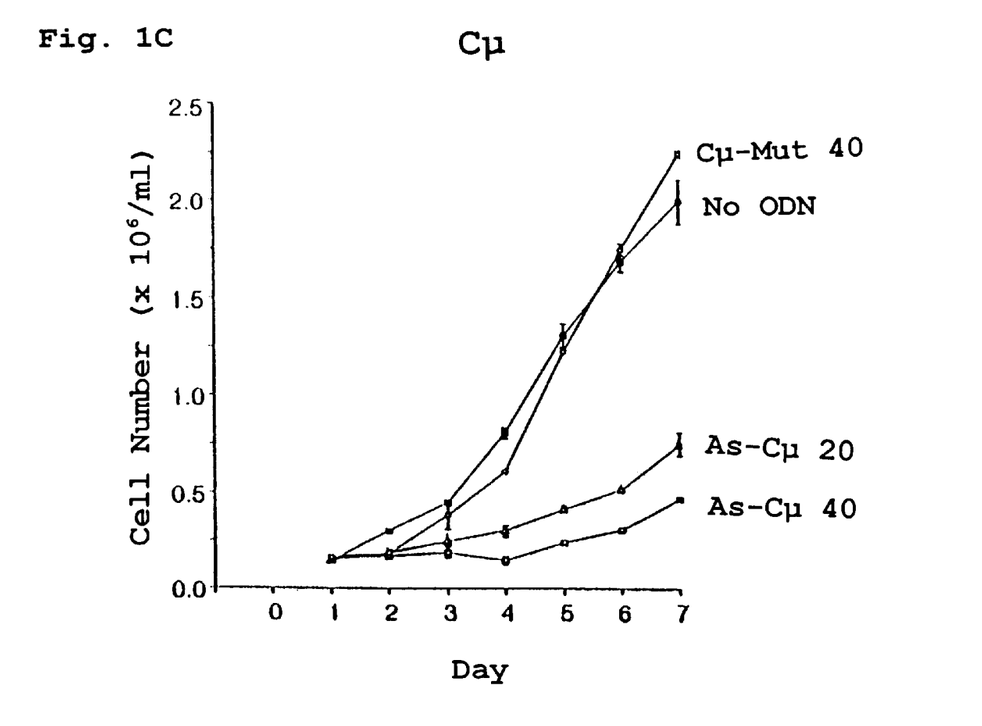
Figure 1D:
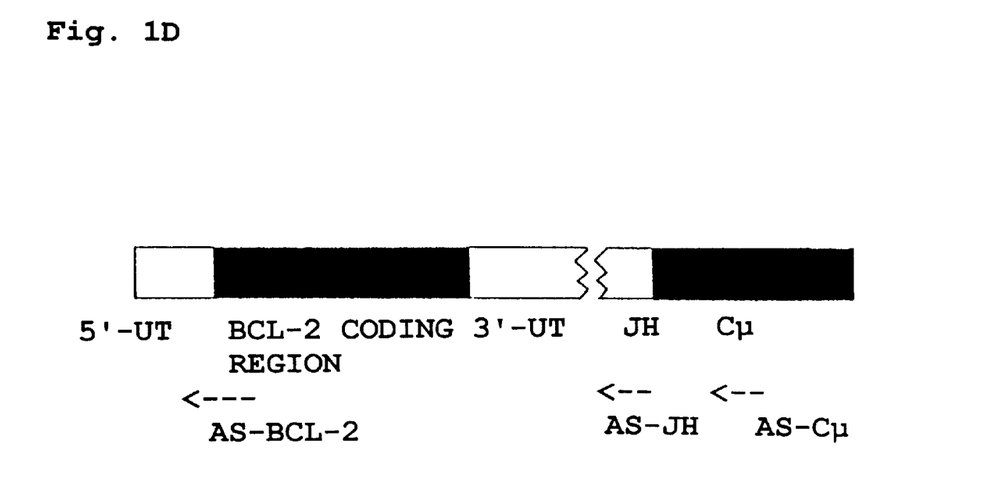
FIG. 1D shows a diagram of the major RNA transcript in WSU-FSCCL with the locations targeted by the antisense oligonucleotides.

RNA analysis (polymerase chain reaction and Northern, not shown) revealed that the major bcl-2 transcript in WSU-FSCCL cells contains bcl-2 fused to $J_H$ and then to $c\mu$, the constant region for the IgM heavy chain. See FIG. 1. Oligonucleotides were designed to target consensus $J_H$ sequences (12) and the $c_H$ $C_H2$ domain (13). Exponentially growing WSU-FSCCL cells plated on day -1 at a cell density of $1.0\times10^5$/ml in 96-well plates were treated with unmodified 17 base oligonucleotides on day 0 to the indicated final concentration (0, 20 or 40 μg/ml). No further additions were made. At the indicated day, cell numbers were determined using a methylthiazole tetrazolium (MTT) assay. (14). Results indicate duplicate wells per experiment for 3 experiments, mean ±S.D. Antisense directed against bcl-2 codons 2 through 7 (FIG. 1A) and $c\mu$ (FIG. 1C) are effective in inhibiting growth, whereas $J_H$ targeted antisense oligonucleotides (FIG. 1B) are less active. Corresponding control oligonucleotides with 8 base changes that retain overall base composition were not cytotoxic.

Sequences of oligonucleotides tested are (5'-3'):
Sequence I.D. No. 1: bcl-2 antisense gttctcccagcgtgcgc (3),
Sequence I.D. No. 2: bcl-2 mut ttgcgcccctagggctc (6),
Sequence I.D. No. 3: $J_H$ antisense ctgaggagacggtgacc (12),
Sequence I.D. No. 4: $J_H$-mut cggatgcgaatgggcca,
Sequence I.D. No. 5: $c\mu$ antisense gaagacgctcactttgg (13),
Sequence I.D. No. 6: $c\mu$ mut gtacaggcactgttagc.

Antisense oligonucleotides to the $c\mu$ $C_H2$ domain inhibited growth of WSU-FSCCL cells to a similar extent as did those targeted to the bcl-2 translational start site, as can be appreciated from FIG. 1. Targeting the consensus $J_H$ sequences had little effect. In each case, control oligonucleotides with 8 base changes that retained the overall base composition, designated mut, did not inhibit growth.

As mentioned previously, other fusion genes may be targeted with antisense oligonucleotides specific for sequences adjacent to chromosomal breakpoints. The following is a series of antisense oligonucleotides directed at such non-oncogenic fusion partner sequences in nucleic acids encoding fusion proteins in malignant cells. Antisense molecules targeted to these sequences represent an additional embodiment of the present invention.

sequences are antisense (5'-3'):
Sequence I.D. No. 7: T cell receptor α cagggtcagggttctgg,
Sequence I.D. No. 8: T cell receptor β cagcgacctcgggtggg,
Sequence I.D. No. 9: Breakpoint cluster region gcgccttccacgcctcc

EXAMPLE II

Figure 2:
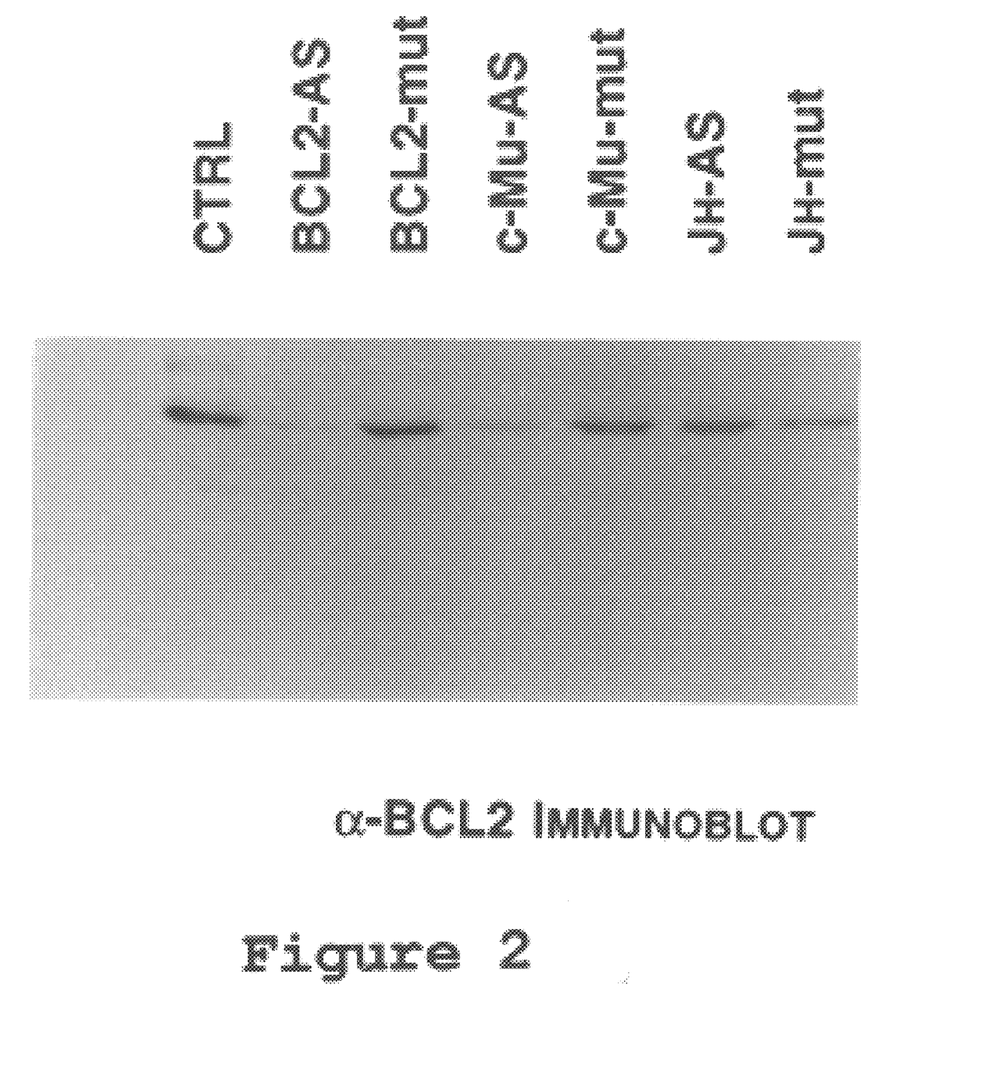
FIG. 2 is an immunoblot showing the inhibition of BCL2 production following administration of various oligonucleotides.
Figure 3A:
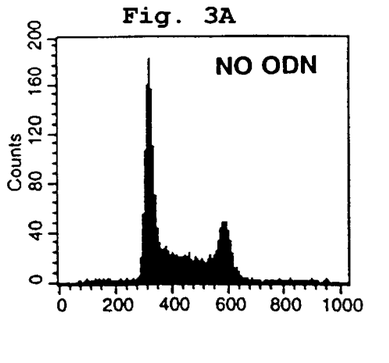
FIG. 3A, negative control.
Figure 3B:
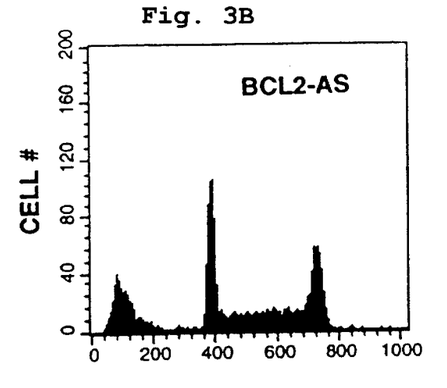
FIG. 3B, bcl-2 antisense oligonucleotide.
Figure 3C:
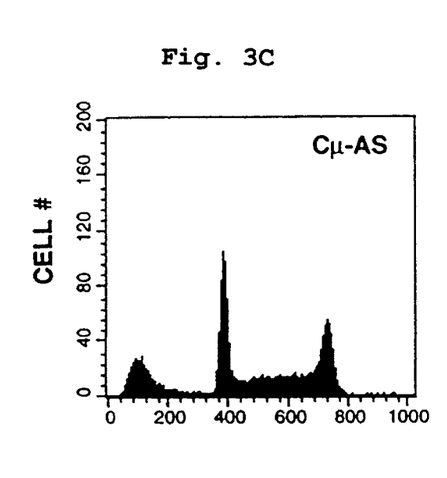
FIG. 3C, $C\mu$ antisense oligonucleotide.
Figure 3D:
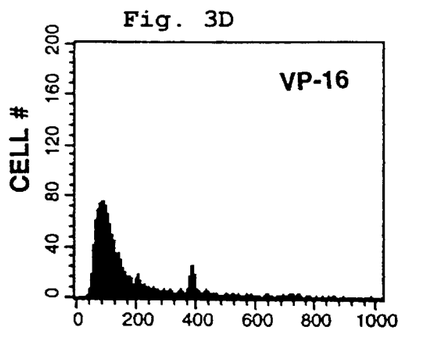
FIG. 3D, VP-16 (etoposide)
Figure 3E:
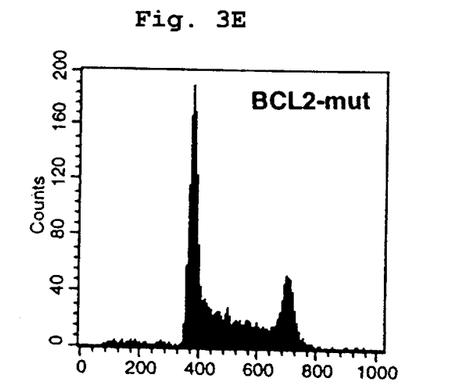
FIG. 3E, mutated bcl-2 antisense oligonucleotide.
Figure 3F:
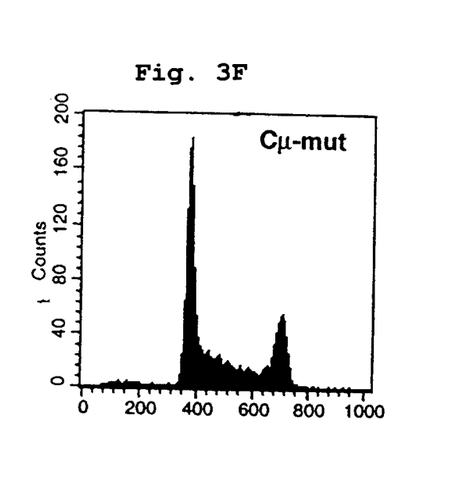
FIG. 3F, mutated $C\mu$ antisense oligonucleotide.

Immunoblots confirm that the oligonucleotides did inhibit BCL2 protein production. Total protein was isolated in a modified RIPA buffer (150 mM NaCl, 1.0% NP-40, 0.5% sodium deoxycholate, 0.1% SDS, 50 mM Tris, pH 8.0), and equal amounts as determined by Bradford dye (Bio-Rad, Hercules, Calif.) were separated by electrophoresis on 4–20% polyacrylamide-SDS gels. Coomassie blue staining confirmed equal loading. Proteins were electrophoretically transferred to 0.45 μM PVDF membrane (Millipore, Bedford, Mass.) which was then pre-treated with 5% non-fat dry milk. Anti-BCL2 antibody (Dako, Carpinteria, Calif.) was added at 1:250 dilution for 60 minutes. Chemiluminescent detection (ECL, Amersham, Little Chalfont, Eng.) of anti-mouse antibody (1:500) was recorded on Kodak XAR film. A representative blot is shown in FIG. 2. The results of quantitative densitometry on four separate experiments are shown in Table I.

TABLE I

QUANTIFICATION OF BCL2 PROTEIN LEVELS ON IMMUNOBLOTS
(% CONTROL, mean ± S.D.)

| AS-BCL-2 | Mut-BCL-2 | AS-C$\mu$ | Mut-C$\mu$ | AS-J$_H$ | Mut-J$_H$ |
|---|---|---|---|---|---|
| 8 ± 7 | 96 ± 6 | 6 ± 1 | 82 ± 5 | 74 ± 5 | 55 ± 3 |

These data confirm that oligonucleotides directed at $c\mu$ immunoglobulin sequences 3' of bcl-2 in the fusion transcript cause down-regulation of BCL2 protein expression. The lack of effect of $J_H$ targeting is not due to its being a consensus sequence since sequence analysis indicated no differences between the consensus sequence and the WSU-FSCCL sequence. Targets in different portions of a gene can show differing efficacy of inhibition, perhaps due to higher order structures in RNA (reviewed in 15).

EXAMPLE III

Antisense c-mμ oligonucleotides prolonged the survival of FSCCL lymphoma-bearing mice. A FSCCL/scid mouse model was developed to demonstrate the feasibility of using antisense oligonucleotides directed at the immunoglobulin portion of BCL2/Ig fusion RNA in vivo. In this model, $1\times10^7$ WSU-FSCCL cells injected intraperitoneally (i.p.) into 4 to 8 week-old female C.B.17 scid mice, results in intra-abdominal tumors and microscopic disease in the liver, spleen, bone marrow and central nervous system. The disease is lethal 8 to 10 weeks post injection of the lymphoma cells. The phosphorothioate-modified oligonucleotides of the invention were assessed for inhibition of tumor development in a scid mouse model. See Table II. Thirty mice were injected i.p. with $1\times10^7$ WSU-FSCCL cells. Twenty-four hours later, the mice were divided into 3 groups of 10 mice each and injected i.p. once weekly with 200 μg phosphorothioate-modified c-mμ antisense oligonucleotide (sequence I.D. No. 5) or c-mµ-mut (mutant) oligonucleotide (sequence I.D. No. 6), or left untreated as controls. All mice in the control and mutated oligonucleotide-treated groups died within 9.5 and 11 weeks after injection of the FSCCL cells. Median survival was 10 weeks in the control group and 10.9 weeks in the mutated oligonucleotide group. All mice in the control and mutant oligonucleotide groups had grossly visible bulky abdominal tumors. Microscopically, lymphoma cells totally replaced the spleen and bone marrow. In the c-mµ antisense-treated group, median survival was prolonged to 16.5 weeks. Two of the mice in this group were still alive beyond 20 weeks post lymphoma cell injection, apparently healthy, with no palpable tumors. Two of the mice that died in this group, had no evident tumor at necropsy, and may have died of infection. The mice in this group that died with tumors had less microscopic tumor in spleen, bone marrow, and liver than did mice dying in the other two groups. Thus, not only did the antisense-treated mice have a significant increase in life span, but also had less tumor burden at the time of death.

TABLE II

| Group (10 mice/group) | c-mu antisense oligonucleotide | c-mu-mutant oligonucleotide | no oligo-nucleotide (control) |
| --- | --- | --- | --- |
| Median survival (weeks) | 16.5 | 10.9 | 10 |

EXAMPLE IV

The expected mechanism of cell growth inhibition by down-regulation of bcl-2 is the induction of apoptosis (16, 17). Cytospin morphology of treated cell populations confirmed that this occurred (not shown). FIG. 3 shows flow cytometric analysis of cells that were treated with the indicated oligonucleotide (80 µg/ml) or 1 µM VP-16 (etoposide) for 48 hours. Cells were lysed in hypotonic solution containing 50 µg/ml propidium iodide (18) and analyzed (FACScan, Becton-Dickinson). Flow cytometric analysis of DNA content demonstrates that antisense, but not mutated, oligonucleotide treatment results in hypodiploid cells as does VP16 treatment. See FIG. 3. Such cells are undergoing programmed cell death (19). Induction of apoptosis when Bcl-2 protein levels decrease may be enhanced in these cells by the presence of a c-myc translocation. Aberrant expression of c-myc can cause apoptosis (20,21), while bcl-2 expression can inhibit this c-myc mediated apoptosis (22,23).

The combined use of chemotherapeutic drugs with the antisense molecules of the present invention for treating malignancy is also contemplated to be within the scope of the invention. As shown in FIG. 3, etoposide (VP16) efficiently induces apoptosis in malignant cells. Antisense molecules of the present invention may be utilized in conjunction with a variety of chemotherapeutic compounds including alkylating agents, (i.e., cyclophosphamide), topoisomerase II directed agents, (i.e., etoposide), anthracyclines, (i.e., doxorubicin), vinca alkaloids, (i.e., vincristine), glucocorticoids, (i.e., dexamethasone), nucleoside analogs, (i.e., fludarabine) and microtubule disrupting agents (i.e., paclitaxel).

While antisense oligonucleotides are designed to be sequence-specific regulators of gene expression, sequence-independent effects, perhaps due to their polyanionic characteristics, have been observed (reviewed in 15,20). A series of oligonucleotides was synthesized for use as negative controls. Effects secondary to sequence motifs such as polyguanosine (reviewed in 15,21) and methylation of CpG (14) have also been described. The active oligonucleotides of the present invention have neither of these motifs and thus may prove to be more effective in the clinic. In addition, efficacy of the oligonucleotides is illustrated by the measurable sequence specific down-regulation of the target protein.

The foregoing results demonstrate that expression from fusion transcripts can be down-regulated by targeting non-oncogenic sequences within the fusion gene. The specific features of t(14;18) that make this an attractive target are that the immunoglobulin genes are contained in the RNA and transient absence of immunoglobulin synthesis is not expected to be harmful. Immunoglobulin supplementation may be provided to patients, if required during treatment with antisense molecules targeted to the cµ sequences. As long as the fusion partner is not itself critical for growth, its down-regulation is likely to be relatively non-toxic to the organism. Whatever the means to down-regulate the gene, e.g. antisense DNA or RNA, or ribozyme, such targeting may prove to be more effective than attempting to target the breakpoint. The breakpoint may be more variable among patients or may lie in a region of the transcript that is not as accessible to the modulating molecule. As the identification of tumor specific fusion transcripts expands, these transcripts will become potential targets for therapy.

The results of the FSCCL/scid mouse model study confirm that in vitro efficacy of antisense c-mu oligonucleotides is also observed in vivo. Such evidence demonstrates the utility of the antisense oligonucleotides of the invention and provides support for the clinical development of antisense oligonucleotides directed at Ig portions of bcl-2/Ig fusion RNA. Refinements in dose and schedule of administration of the oligonucleotides, as well as in backbone design or delivery systems, should yield improved results. A recent study (24) utilized fully phosphorothioated antisense oligonucleotides targeted to the first 6 codons of bcl-2 mRNA to treat human lymphoma patients. Delivery of antisense oligonucleotides to Ig portions of bcl-2/Ig fusion RNA may be effected by the subcutaneous injection method used in that study.

The methodology described in the above examples may be utilized to target other fusion transcripts. Other such targets are set forth in Table III.

TABLE III

POTENTIAL TRANSLOCATION SITES FOR ANTISENSE THERAPY

| DISEASE | TRANSLOCATION | GENES |
| --- | --- | --- |
| CML & Ph+-ALL | t(9,22) | breakpoint cluster region |
| AML-M3 | t(15,17) | PML; Retinoic acid receptorα |
| AML-M4 eos | inv 16 | CBFβ,MYH11 |
| T-ALL | internal deletion of TAL1 | SIL |
| T-cell leukemia or lymphoma | many | TCRα, δ; TCRβ |
| ALCL | t(2,5) | nucleophosmin, ALK |
| Aveolar rhabdo-myosarcoma | t(2,13) | PAX3; FKHR |
| AML | t(8,21) | AML1:ETO |
| MDS | t(3,21) | AML1;EV11 |
| AML | t(6,9) | DEK;CAN |

TABLE III-continued

| | | |
|---|---|---|
| Acute Leukemia | 11q23 | MLL |
| Pre-B-ALL | t(1,19) | E2A;PBX |
| | t(17,19) | E2A;HLF |
| CMMoL | t(5,12) | PDGFRβ;TEL |

The following list provides definitions for the abbreviations in Table III:

| | |
|---|---|
| CML | chronic myelogenous leukemia |
| Ph+-ALL | Philadelphia chromosome positive acute lymphocytic leukemia |
| AML-M3 | acute myelogenous leukemia, subtype M3; acute promyelocytic leukemia |
| AML-M4eos | acute myelogenous leukemia, subtype M4 with eosinophilia |
| T-ALL | T cell acute lymphocytic leukemia |
| ALCL | anaplastic large cell lymphoma |
| AML | acute myelogenous leukemia |
| MDS | myelodysplastic syndrome |
| Pre-B-ALL | precursor B cell acute lymphocytic leukemia |
| CMMol | chronic myelomonocytic leukemia |
| inv | inversion of a chromosome segment |
| t(m,n) | translocation between chromosome m and n |
| TAL1 | T cell acute leukemia 1 gene |
| PML | promyelocytic leukemia gene |
| CBFβ | core binding factor β |
| MYH11 | myosin heavy chain |
| SIL | SCL (stem cell leukemia)-interrupting locus |
| TCR | T cell receptor |
| ALK | anaplastic large cell kinase |
| PAX3 | paired box gene-3 |

Solid tumors containing fusion sequences in addition to hematopoietic neoplasms, may also be targeted with the antisense molecules of the present invention. Several examples are provided below.
myxoid liposarcoma t(12,16)
TLS (translocated liposarcoma)/CHOP (CCAAT/enhancer binding protein homologous protein)
Ewing's sarcoma t(11,22)
EWS (Ewing's sarcoma)/FLI1 (Friend leukemia virus integration site 1)
gastric tumors not defined
tpr (translocated promoter region)/met (MNNNG-HOS transforming gene)
thyroid tumors not defined
tpr (see above))/trk (tropomyosin receptor kinase)

REFERENCES

1. Bakhshi, A., Jensen, J. P., Wright, J. J. McBride, O. W., Epstein, A. L. & Korsmeyer, S. J. Cell 41: 899–906 (1985).
2. Tsujimoto, Y. & Croce, C. M. Proc. Natl. Acad. Sci. USA 53: 5214–5218 (1986).
3. Cleary, M. L., Smith, S. D. & Sklar, J. Cell 47: 19–28 (1986).
4. Reed, J. C., Stein, C. Subasinghe, C., Haldar, S., Croce., C. M., Yum, S. & Cohen, J. Cancer Res. 50: 6565–6570 (1990).
5. Cotter, F. E., Johnson, P., Hall, P., Pocock, C., Al Mahdi, N., Cowell, J. K. & Morgan, G. Oncogene 9: 3049–3055 (1994).
6. Smith, M. R., Abubakr, Y., Mohammad, R., Xie, T., Hamdan, M. & Al-Katib, A. Cancer Gene Ther. 2: 207–212 (1995).
7. Weiss, L. M., Warnke, R. A., Sklar, J. & Cleary, M. L. N. Eng. J. Med. 317: 1185–11 (1987).
8. Ngan, B-Y., Nourse, J. & Cleary, M. L. Blood 73: 1759–1762 (1989).
9. Graninger, W. B., Seto, M., Boutain, B., Goldman, P. & Korsmeyer, S. J. J. Clin. Invest. 80: 1512–1515 (1987).
10. Seto, M., Jaeger, U., Hockett, R. D., Graninger, W., Bennett, S., Goldman, P. & Korsmeyer, S. J. EMBO J. 7: 123–131 (1988).
11. Marshall, W. S. & Caruthers, M. H. Science 259: 1564–70 (1993).
12. Crescenzi, M., Seto, M., Herzig, G. P., Weiss, P. D. & Griffith, R. C. Proc. Natl. Acad. Sci. 85: 4869–4873 (1988).
13. Dorai, H. & Gillies, S. D. Nucl. Acids Res. 17: 6412 (1989).
14. Hansen, M. B., Nielson, S. E. & Berg, K. J. Immunol. Meth. 119: 203–210 (1989).
15. Stein, C. A. & Cheng, Y-C. Science 261: 1004–1012 (1993).
16. Kitada, S., Takayama, S., deRiel, K., Tanaka, S. & Reed, J. C. Antisense Res. Dev. 4: 71–79 (1994).
17. Keith, F. J., Bradbury, D.A., Zhu, Y-M. & Russell, N.H. Leuk. 9: 131–138 (1995).
18. Freid, J., Perez, A. G. & Clarkson, B. D. J. Histochem. Cytochem. 26: 921–933, 1978.
19. Nicoletti, I., Migliorati, G., Pagliacci, M. C., Grignani, F.& Riccardo, C. J. Immunol. Meth. 139: 271–279 (1991).
20. Wagner, R. W. Nature 372: 333–335 (1994).
21. Krieg, A. M., Yi, A-K., Matson, S., Waldschmidt, T. J., Bishop, G. A., Teasdale, R., Koretsky, G. A. & Klinman, D. M. Nature 374: 546–549 (1995).
22. Bissonnette, R. P., Echeverri, F., Mabboubi, A. & Green, D. R. Nature 359: 552–554 (1992).
23. Fanidi, A., Harrington, E. A. & Evan, G. 1. Nature 359: 554–556 (1992).
24. Webb, A., Cunningham, D., Cotter, F., Clarke, P. A., di Stefano, F., Ross, P., Corbo, M., Dziewanowska, Z. The Lancet 349: 1137–1141, 1997.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. An antisense oligonucleotide having the sequence of SEQ ID NO:5 for inhibiting production of a predetermined fusion protein in a malignant cell expressing a fusion protein transcript, said antisense oligonucleotide, following entry into said cell, binding specifically to a non-oncogenic fusion sequence of a nucleic acid that encodes said fusion transcript, thereby inhibiting production of said fusion protein.

2. An analog of the antisense oligonucleotide as claimed in claim 1, said analog being selected from the group consisting of peptide nucleic acids, methylphosphonates and 2-O-methyl ribonucleic acids.

3. A phosphorothioate analog of the antisense oligonucleotide as claimed in claim 1.

4. A vector comprising a DNA which encodes the antisense oligonucleotide of claim 1.

5. A pharmaceutical preparation for treating a pathological condition related to the expression by cells of an aberrant fusion protein, which comprises an antisense oligonucleotide analog which enters said cells expressing said fusion protein and binds specifically to a nucleic acid molecule encoding said fusion protein, said antisense oligonucleotide being present in a biologically compatible medium and having the sequence of SEQ ID NO: 5.

6. A pharmaceutical preparation according to claim 5, wherein said antisense oligonucleotide binds specifically to a sequence adjacent to a chromosomal translocation breakpoint.

7. A pharmaceutical preparation according to claim 5, which further comprises at least one agent for improving delivery of said antisense oligonucleotide to said cells expressing said fusion protein.

8. A pharmaceutical preparation according to claim 7, wherein said at least one agent comprises a lipid.

9. A pharmaceutical preparation according to claim 8, wherein said antisense oligonucleotide is encapsulated in a lipid vessicle.

10. A pharmaceutical preparation according to claim 5, which further comprises at least one targeting agent for improving cell-type specific delivery of said antisense oligonucleotide.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
    (A) LENGTH: 17 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:1:

GTTCTCCCAG CGTGCGC               17

(2) INFORMATION FOR SEQ ID NO:2:

(i) SEQUENCE CHARACTERISTICS:
    (A) LENGTH: 17 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:2:

TTGCGCCCCT AGGGCTC               17

(2) INFORMATION FOR SEQ ID NO:3:

(i) SEQUENCE CHARACTERISTICS:
    (A) LENGTH: 17 base pairs
    (B) TYPE: nucleic acid
    (C) STRANDEDNESS: single
    (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:3:

CTGAGGAGAC GGTGACC               17

(2) INFORMATION FOR SEQ ID NO:4:

(i) SEQUENCE CHARACTERISTICS:
    (A) LENGTH: 17 base pairs
    (B) TYPE: nucleic acid
    (C) STRANDEDNESS: single
    (D) TOPOLOGY: Not Relevant -continued (ii) MOLECULE TYPE: DNA (genomic)

(iii) HYPOTHETICAL: NO (iv) ANTI-SENSE: YES (xi) SEQUENCE DESCRIPTION: SEQ ID NO:4:

CGGATGCGAA TGGGCCA

17

(2) INFORMATION FOR SEQ ID NO:5:

(i) SEQUENCE CHARACTERISTICS:
            (A) LENGTH: 17 base
pairs
            (B) TYPE: nucleic acid
            (C) STRANDEDNESS: single
            (D) TOPOLOGY: Not Relev
ant (ii) MOLECULE TYPE: DNA (genomic)

(iii) HYPOTHETICAL: NO (iv) ANTI-SENSE: YES (xi) SEQUENCE DESCRIPTION: SEQ ID NO:5:

GAAGACGCTC ACTTTGG

17

(2) INFORMATION FOR SEQ ID NO:6:

(i) SEQUENCE CHARACTERISTICS:
            (A) LENGTH: 17 base
pairs
            (B) TYPE: nucleic acid
            (C) STRANDEDNESS: single
            (D) TOPOLOGY: Not Relev
ant (ii) MOLECULE TYPE: DNA (genomic)

(iii) HYPOTHETICAL: NO (iv) ANTI-SENSE: YES (xi) SEQUENCE DESCRIPTION: SEQ ID NO:6:

GTACAGGCAC TGTTAGC

17

(2) INFORMATION FOR SEQ ID NO:7:

(i) SEQUENCE CHARACTERISTICS:
            (A) LENGTH: 17 base
pairs
            (B) TYPE: nucleic acid
            (C) STRANDEDNESS: single
            (D) TOPOLOGY: Not Relev
ant (ii) MOLECULE TYPE: DNA (genomic)

(iii) HYPOTHETICAL: NO (iv) ANTI-SENSE: YES (xi) SEQUENCE DESCRIPTION: SEQ ID NO:7:

CAGGGTCAGG GTTCTGG

17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: Not Relevant     (ii) MOLECULE TYPE: DNA (genomic)

(iii) HYPOTHETICAL: NO

(iv) ANTI-SENSE: YES

(xi) SEQUENCE DESCRIPTION: SEQ ID NO:8:

CAGCGACCTC GGGTGGG

17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: Not Relevant     (ii) MOLECULE TYPE: DNA (genomic)

(iii) HYPOTHETICAL: NO

(iv) ANTI-SENSE: YES

(xi) SEQUENCE DESCRIPTION: SEQ ID NO:9:

GCGCCTTCCA CGCCTCC

17